(12) United States Patent
Umemoto et al.

(10) Patent No.: US 10,596,044 B2
(45) Date of Patent: Mar. 24, 2020

(54) METHOD OF MANUFACTURING ABSORBENT ARTICLE

(71) Applicant: DAIO PAPER CORPORATION, Ehime (JP)

(72) Inventors: Kaori Umemoto, Tochigi (JP); Yoko Suzuki, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 243 days.

(21) Appl. No.: 15/106,362

(22) PCT Filed: Dec. 26, 2014

(86) PCT No.: PCT/JP2014/084507
§ 371 (c)(1),
(2) Date: Jun. 20, 2016

(87) PCT Pub. No.: WO2015/099121
PCT Pub. Date: Jul. 2, 2015

(65) Prior Publication Data
US 2017/0027765 A1 Feb. 2, 2017

(30) Foreign Application Priority Data

Dec. 26, 2013 (JP) ................................ 2013-268306

(51) Int. Cl.
*A61F 13/15* (2006.01)
*A61F 13/536* (2006.01)
(Continued)

(52) U.S. Cl.
CPC .. *A61F 13/15804* (2013.01); *A61F 13/15699* (2013.01); *A61F 13/15707* (2013.01);
(Continued)

(58) Field of Classification Search
CPC .......... A61F 13/15804; A61F 13/15699; A61F 13/15707; A61F 13/15747; A61F 13/47;
(Continued)

(56) References Cited

U.S. PATENT DOCUMENTS 6,692,603 B1 * 2/2004 Lindsay ............ A61F 13/15707
156/209
2004/0055694 A1 3/2004 Kershaw et al.
(Continued)

FOREIGN PATENT DOCUMENTS

EP 2277484 1/2011
JP S54-035599 U 3/1979
(Continued)

OTHER PUBLICATIONS

Japanese Office Action dated Jun. 21, 2016.
International Search Report dated Mar. 17, 2015.

*Primary Examiner* — Matthew J Daniels
*Assistant Examiner* — Andrew L Swanson
(74) *Attorney, Agent, or Firm* — IPUSA, PLLC

(57) ABSTRACT

A method of manufacturing an absorbent article. The method includes a first step of forming the absorbent body provided with the absorbent body concave portion; a second step of forming core embosses at least on both sides of the absorbent body concave portion by compressing the absorbent body from the skin-contacting side of the absorbent body; and a third step of stacking the liquid permeable topsheet on a top surface side of the absorbent body and forming the embossed portion.

11 Claims, 6 Drawing Sheets

(51) Int. Cl.
*A61F 13/511* (2006.01)
*A61F 13/47* (2006.01)
*B29C 59/00* (2006.01)
*B29C 59/02* (2006.01)
*B29C 65/48* (2006.01)
*B29K 105/08* (2006.01)
*B29L 31/48* (2006.01)

(52) U.S. Cl.
CPC ........ *A61F 13/15747* (2013.01); *A61F 13/47* (2013.01); *A61F 13/51108* (2013.01); *A61F 13/536* (2013.01); *B29C 59/007* (2013.01); *B29C 59/025* (2013.01); *B29C 65/4815* (2013.01); *A61F 2013/15715* (2013.01); *B29K 2105/0809* (2013.01); *B29K 2995/0068* (2013.01); *B29L 2031/4878* (2013.01)

(58) Field of Classification Search
CPC .............. A61F 13/51108; A61F 13/536; A61F 2013/15715; A61F 13/511; A61F 13/51104; A61F 13/512; A61F 13/51311; A61F 13/51355; A61F 13/51383; B29C 59/007; B29C 59/025; B29C 65/4815; B29K 2105/0809; B29K 2995/0068; B29L 2031/4878

See application file for complete search history.

(56) References Cited

U.S. PATENT DOCUMENTS

| 2006/0069371 | A1* | 3/2006 | Ohashi | A61F 13/4704 |
| | | | | 604/385.01 |
| 2009/0005752 | A1* | 1/2009 | Suzuki | A61F 13/494 |
| | | | | 604/385.101 |

FOREIGN PATENT DOCUMENTS

| JP | S5435599 B2 * | 11/1979 |
| JP | 2003-024376 | 1/2003 |
| JP | 2004-298330 | 10/2004 |
| JP | 2005-087655 | 4/2005 |
| JP | 2006-095156 | 4/2006 |
| JP | 2007-089907 | 4/2007 |
| JP | 2008-080150 | 4/2008 |
| JP | 2008080150 A * | 4/2008 |
| JP | 2009-112590 | 5/2009 |
| JP | 2009112590 A * | 5/2009 |
| JP | 2013-075009 | 4/2013 |

* cited by examiner

METHOD OF MANUFACTURING ABSORBENT ARTICLE

BACKGROUND OF THE INVENTION

1. Field of the Invention

The present invention mainly relates to a method of manufacturing an absorbent article used in incontinence pads, sanitary napkins, panty liners, medical pads, toiletries, disposal diapers and the like, and a method of manufacturing an absorbent article including an absorbent body having a concave groove formed at a top surface thereof along a longitudinal direction thereof.

2. Description of the Related Art

In conventional absorbent articles, an absorbent body is provided between a liquid impermeable backsheet, such as a polyethylene sheet or a non-woven fabric made of laminated polyethylene sheets, and a liquid permeable topsheet, such as a non-woven fabric or a permeable plastic sheet.

This kind of absorbent article has been improved many times, and various means are provided in order to prevent leakage of body fluid. As one of the means to prevent leakage of body fluid, a technique is provided to form a concave groove by heat embossing. For example, Patent Document 1 describes an absorbent article for increasing absorbance and retaining characteristics of liquid or the like, and suppressing or preventing flowback or leakage of the liquid or the like by quickly transferring the liquid or the like once absorbed to inside an absorbent body. For such purposes, Patent Document 1 describes a middle high portion formed by an upper absorbent layer and a lower absorbent layer provided with a groove formed in a skin contacting side and extending in a longitudinal direction of the absorbent article. The groove is an opening portion penetrating through the upper absorbent layer, and the lower absorbent layer is located under the lower surface of the upper absorbent layer so as to form a bottom surface of the opening portion. Further, Patent Document 2 describes a ladies' incontinence pad capable of suppressing swelling of an absorbent body near a standing gather due to absorption of urine by the absorbent polymer, by forming emboss processed portions along the standing gather near the inside of the standing gather of the absorbent body and at a using surface side of the absorbent body. Further, Patent Document 3 describes an absorbent article including a liquid permeable topsheet made of a sheet provided with a plurality of openings or a non-woven fabric. The absorbent article includes a center emboss, which is a concave groove, formed in the absorbent body from an upper surface of the liquid permeable topsheet and side embosses on both sides of the center emboss. The center emboss is processed after the side embosses are formed as a post-treatment so that the concave groove is formed at a center emboss processed portion while the liquid permeable topsheet is stretched and the opening of the topsheet is enlarged or the spaces between the fibers of the non-woven fabric are enlarged at the center emboss processed portion.

PATENT DOCUMENTS

Patent Document 1: Japanese Laid-open Patent Publication No. 2009-112590
Patent Document 2: Japanese Laid-open Patent Publication No. 2005-87655
Patent Document 3: Japanese Patent No. 4,652,626

According to the absorbent article of Patent Document 1, the upper layer absorbent body is stacked on the lower layer absorbent body, and a part (a bottom surface of the open portion) of the lower layer absorbent body at a top surface side directly stick to the topsheet at the open portion. Then, at least the part of the bottom surface of the open portion of the lower layer absorbent body is bonded to the part of the topsheet that is introduced therein via the open portion by a melt adhesive method.

As such, when bonding the topsheet with the bottom surface of the open portion of the lower layer absorbent body by introducing a part of the topsheet in the open portion by pressing from the top surface side of the topsheet, the following problems occurred. Uniform products cannot be manufactured due to problems such as (1) the absorbent body is clipped between rollers and the side walls of the open portion are fallen down inside while line transferring the absorbent body and the fallen absorbent body is also compressed when the topsheet is pressed, (2) a part of the absorbent body around the open portion is compressed because shifts in a front and rear direction and a left and right direction in transferring occur while line transferring the absorbent body and aligning the open portion with the pressing position becomes difficult.

Furthermore, in order to solve such problems, a measure may be considered in which the open portion of the absorbent body is formed large. However, if the open portion is made large, it is necessary to increase the mass per unit area of the absorbent body around the open portion in order to compensate the absorbance. As a result, the thickness of the product is increased, which worsens fittability.

Further, if the emboss is formed inside the concave groove by the compression from the top surface side of the liquid permeable topsheet after stacking the liquid permeable topsheet at the top surface side of the absorbent body in which the concave groove is pre-formed, there is a case that side walls of the concave groove fall down inside in accordance with the compression to the bottom portion of the concave groove. With this, a problem that the volume of the concave groove is decreased, thereby reducing the amount of the body fluid reserved therein occurs.

On the other hand, the body fluid temporarily reserved in the open portion penetrates the absorbent body from the side walls of the open portion. However, for the product in which the density of the absorbent body around the open portion is uniquely formed, the body fluid penetrated the absorbent body from the side walls of the open portion tends to stay there and the water retention capacity of the absorbent body easily becomes full. As a result, there is a risk that the water cannot be further absorbed.

Here, as described in Patent Document 3, although a technique to enlarge a plurality of openings formed at the liquid permeable topsheet by performing emboss processing has been known, there is no technique to enlarge the opening of the concave portion formed in the absorbent body.

SUMMARY OF THE INVENTION

The main problem to be solved by the present invention is to provide a method of manufacturing an absorbent article by which a concave groove can be easily processed, the concave groove can be properly formed, fittability is not worsened, and diffusion of body fluid is improved.

As the invention of claim 1 to solve the above described problem, there is provided a method of manufacturing an absorbent article in which an absorbent body is provided between a liquid permeable topsheet and a backsheet, an absorbent body concave portion, which is a concave groove or a slit, being formed at a skin-contacting side including a body fluid expelling area along a longitudinal direction of the absorbent body without using compression, and an embossed portion being formed in the absorbent body concave portion along the absorbent body concave portion by embossing from a top surface side of the liquid permeable topsheet, the method including a first step of forming the absorbent body provided with the absorbent body concave portion; a second step of forming core embosses at least on both sides of the absorbent body concave portion by compressing the absorbent body from the skin-contacting side of the absorbent body; and a third step of stacking the liquid permeable topsheet on a top surface side of the absorbent body and forming the embossed portion.

The invention of claim 1 is a method of manufacturing an absorbent article in which an absorbent body is provided between a liquid permeable topsheet and a backsheet, an absorbent body concave portion, which is a concave groove or a slit, being formed at a skin-contacting side including a body fluid expelling area along a longitudinal direction of the absorbent body without using compression, and an embossed portion being formed in the absorbent body concave portion along the absorbent body concave portion by embossing from a top surface side of the liquid permeable topsheet. In such an absorbent article, by pre-forming the absorbent body concave portion in the absorbent body, even when body fluids that flow into the concave groove penetrate the absorbent body, and the polymer and pulp around the absorbent body concave portion expand, rising up of the bottom surface of the absorbent body concave portion can be suppressed to be extremely small compared with a case in which the polymer and pulp that are made to be high density by the compression. Furthermore, as the liquid permeable topsheet exists in the absorbent body concave portion by the embossed portion, expansion of the side surfaces of the absorbent body concave portion can also be suppressed to be small. Thus, lowering of the absorbance of the body fluid due to blockage of the absorbent body concave portion by the expanded polymer and pulp that has absorbed the fluid can be prevented. Meanwhile, when the absorbent body concave portion is formed as a slit, as the absorbent body does not exist at a bottom surface of the absorbent body concave portion, the bottom surface does not expand when absorbing the fluid.

When manufacturing such an absorbent article, according to the invention, manufacturing steps including a first step of forming the absorbent body provided with the absorbent body concave portion, a second step of forming core embosses at least on both sides of the absorbent body concave portion by compressing the absorbent body from the skin-contacting side of the absorbent body, and a third step of stacking the liquid permeable topsheet on a top surface side of the absorbent body and forming the embossed portion are used. By forming the core embosses in the second step, as the side walls of the absorbent body concave portion are inclined outward by being pulled by these core embosses, the opening of the absorbent body concave portion is enlarged. Thus, when providing the embossed portion from the top surface side of the liquid permeable topsheet in the next third step, a front end portion of an embossing machine can be easily introduced inside the absorbent body concave portion, the absorbent body and the embossing machine can be easily aligned so that the concave groove can be easily processed, and the concave groove can be properly formed without compressing unnecessary portions.

Further, as the concave groove can be formed without increasing the opening size of the absorbent body concave portion, and it is unnecessary to increase mass per unit area or the thickness of the absorbent body, fittability of the absorbent article can be retained.

Further, as the core embosses that are densely compressed are formed near the absorbent body concave portion, when the body fluid that is temporarily reserved in the absorbent body concave portion penetrates the absorbent body, the body fluid tends to be introduced toward the core embosses due to the density gradient of fibers so that the diffusion of the body fluid is improved and the absorbance can be improved.

As the invention of claim 2, there is provided the method of manufacturing the absorbent article according to claim 1, wherein each of the core embosses is formed at a distance range from an edge portion of the absorbent body concave portion that is greater than or equal to 10 mm and less than or equal to 30 mm.

According to the invention of claim 2, each of the core embosses is formed at a distance range from an edge portion of the absorbent body concave portion that is greater than or equal to 10 mm and less than or equal to 30 mm. If the core emboss is formed at a distance less than 10 mm, the height (depth) of the absorbent body concave portion is reduced due to pulling by the core embosses, which reduces the volume of the concave groove and there is a risk that absorbance of the body fluid is lowered. Further, if the core emboss is formed at a distance greater than 30 mm, it is not preferable because the effect of tilting the side walls of the absorbent body concave portion outward may be reduced.

As the invention of claim 3, there is provided the method of manufacturing the absorbent article according to claim 1 or 2, wherein the plane shape of each of the core embosses is a pattern of one or a plurality of continuous lines or discontinuous lines, or dots or a grid-like shape along a longitudinal direction of the absorbent article.

According to the invention of claim 3, it is defined that it is preferable that the plane shape of each of the core embosses is a pattern of one or a plurality of continuous lines or discontinuous lines, or dots or a grid-like shape along a longitudinal direction of the absorbent article. Here, the continuous line or the discontinuous line may be linear or curved such as an arc or the like.

As the invention of claim 4, there is provided the method of manufacturing the absorbent article according to one of claims 1 to 3, wherein the core embosses are also formed at a front side and a rear side of the absorbent body concave portion.

According to the invention of claim 4, by forming the core embosses at a front side and a rear side of the absorbent body concave portion as well, the absorbance can be further improved because the diffusion of the body fluid penetrated in the absorbent body from the concave groove toward the front side and the rear side can be improved.

As the invention of claim 5, there is provided the method of manufacturing the absorbent article according to one of claims 1 to 4, wherein the core emboss is continuously or discontinuously formed from an absorbent body concave portion side toward the outer side in a plan view, and the compression pressure is set such that the compression pressure gradually increases toward the outer side.

According to the invention of claim 5, when forming each of the core embosses continuously or discontinuously from an absorbent body concave portion side toward the outer side in a plan view, by setting the compression pressure such that the compression pressure gradually increases toward the outer side, the density gradient of the absorbent body is gradually increased toward the outer side. Thus, the diffusion of the body fluid is further increased and the absorbance is improved.

As described above in detail, according to the invention, a concave groove can be easily processed, the concave groove can be properly formed, fittability is not worsened, and diffusion of body fluid is improved.

DETAILED DESCRIPTION OF THE PREFERRED EMBODIMENTS

Next, embodiments of the present invention will be described below with reference to drawings.
(Basic Structure of Incontinence Pad 1)

Figure 1:
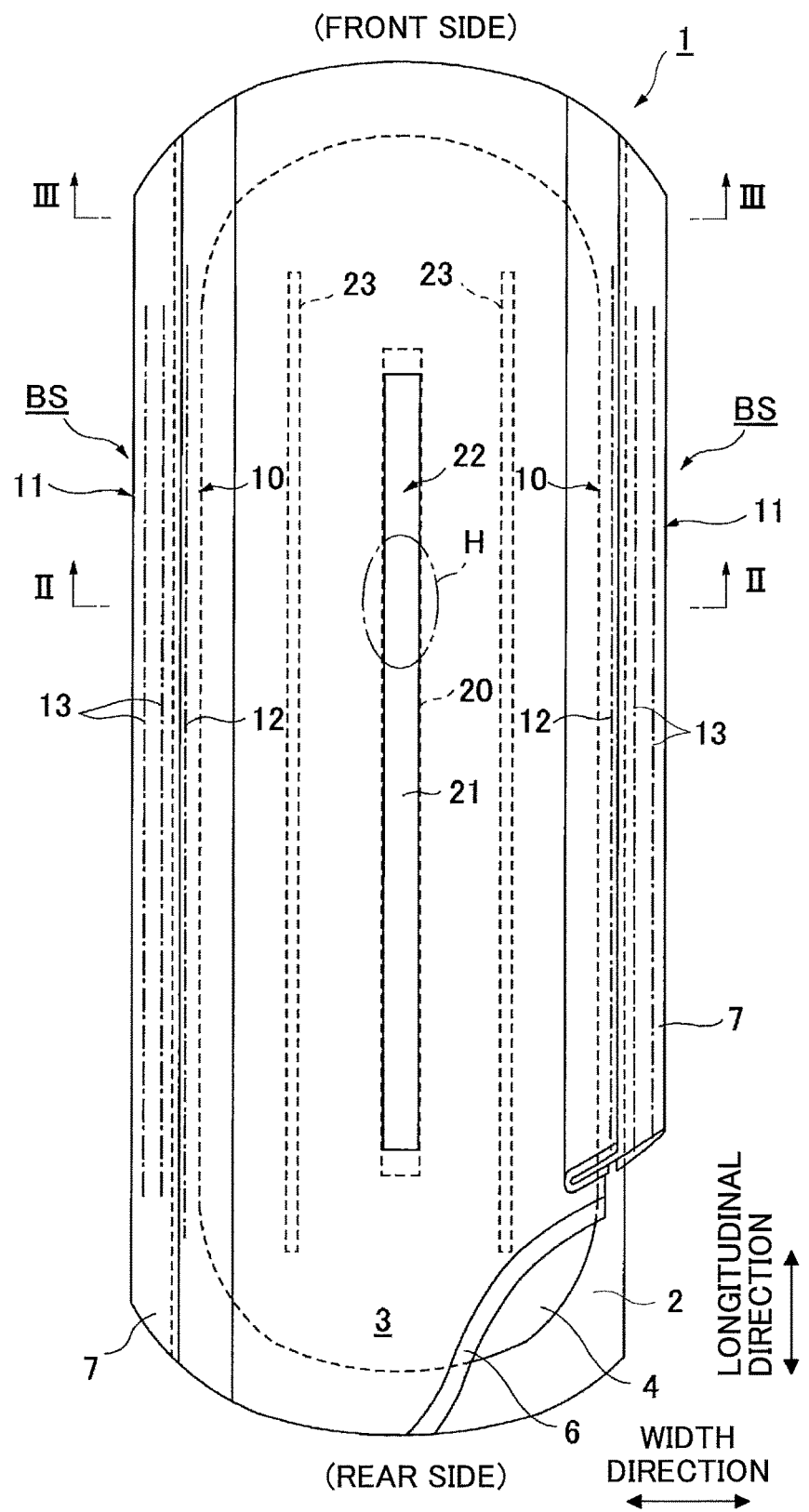
FIG. 1 is a partially broken developed view of an incontinence pad 1 of the invention.
Figure 2:
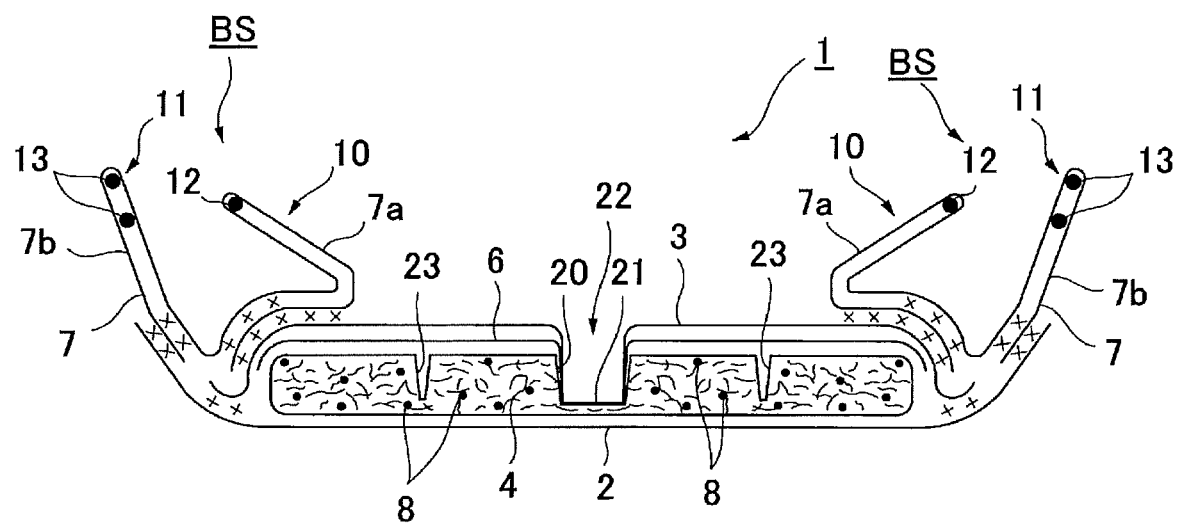
FIG. 2 is a cross-sectional view taken along a II-II line of FIG. 1.
Figure 3:
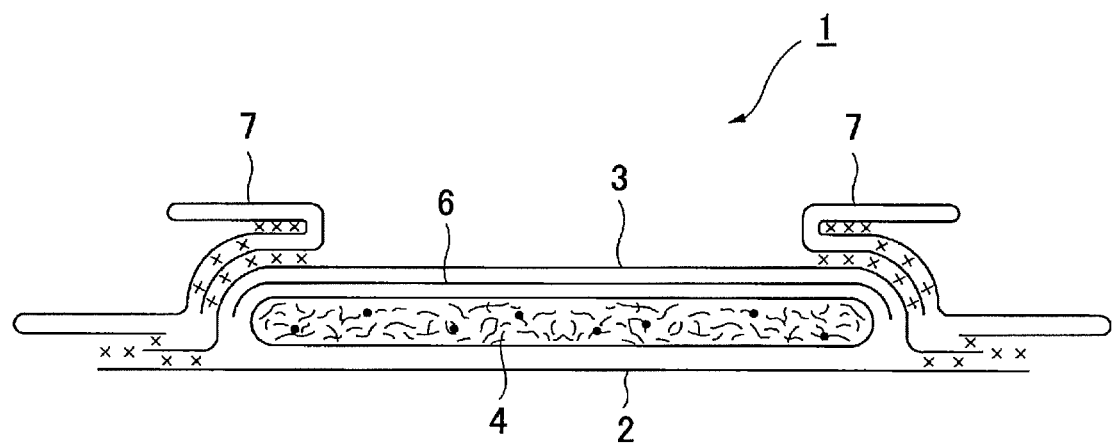
FIG. 3 is a cross-sectional view taken along a III-III line of FIG. 1.

As illustrated in FIG. 1 through FIG. 3, an incontinence pad 1 of the present invention is mainly constituted of a liquid impermeable backsheet 2 made of polyethylene, a liquid permeable topsheet 3 that allows urine and the like to rapidly permeate, an absorbent body 4 made of cotton-like pulp, synthetic pulp, or the like, and that is provided between both the sheets 2 and 3, a hydrophilic second sheet 6 disposed between the liquid permeable topsheet 3 and the absorbent body 4, as necessary, and side non-woven fabrics 7, 7 forming a matched pair of standing gathers BS that protrude toward a skin side in a predetermined zone including at least a body fluid expelling area H in the longitudinal direction, while standing from approximately side edge parts of the absorbent body 4. Around the absorbent body 4, the outer end portions of the liquid impermeable backsheet 2 and the liquid permeable topsheet 3 are bonded with an adhesive such as a hot-melt adhesive or an adhesive means such as a heat seal and the like at end portions in the longitudinal direction, and the liquid impermeable backsheet 2 laterally protruding from the absorbent body 4 and the side non-woven fabrics 7 are bonded with the adhesive such as the hot-melt adhesive or the adhesive means such as the heat seal and the like at the edge portions on both sides. The absorbent body 4 can be surrounded by an encapsulating sheet such as a crepe paper sheet, a non-woven fabric or the like to retain a shape and to improve diffusivity of the absorbent body 4.

Hereinafter, the structure of the incontinence pad 1 is further described in more detail. A sheet material having at least water shielding properties such as polyethylene, polypropylene or the like is used in the liquid impermeable backsheet 2. In addition to this, a non-woven fabric sheet can be also used after ensuring substantial impermeability by providing a waterproof film to cover the non-woven fabric sheet (in this case, the liquid impermeable backsheet is composed of the waterproof film and the non-woven fabric sheet). In recent years, a material having moisture permeability is often preferably used to prevent sweating. A microporous sheet obtained by forming a sheet by melting and kneading inorganic filler in olefin series resin such as polyethylene and polypropylene and then extruding the sheet in one axial direction or two axial directions, is preferably used as the waterproof and moisture permeable sheet material.

Next, a perforated or imperforate non-woven fabric or a porous plastic sheet is preferably used as the liquid permeable topsheet 3. For example, a regenerated fiber such as rayon and cupra, and a natural fiber such as cotton, can be used as a material fiber forming the non-woven fabric in addition to a synthetic fiber including an olefin series such as polyethylene and polypropylene, a polyester series, a polyamide series and the like. As the non-woven fabric, a non-woven fabric obtained by a proper processing method such as a spun lace method, a spun bond method, a thermal bond method, a melt blown method, and a needle punch method, can be used. Among the processing methods, the spun lace method is superior in terms of great flexibility and drape properties, and the thermal bond method is superior in terms of bulkiness and softness.

The absorbent body 4 is, for example, constituted of an absorbable fiber such as a fluff pulp and superabsorbent polymers 8, and is formed into an approximately oval shape extending long in a longitudinal direction of the pad in a planar shape in the illustrated example. The superabsorbent polymers 8 are, for example, formed into granular powders, and are diffused and mixed into the pulp forming the absorbent body 4.

Chemical pulp obtained from wood, a cellulose fiber such as dissolving pulp, and an artificial cellulose fiber such as rayon and acetate, are cited as examples available for the pulp, and softwood pulp having a fiber length longer than that of hardwood pulp is preferably used in terms of function and price. In this incontinence pad 1, as the absorbent body 4 is surrounded by the encapsulating sheet 5, as a result, the encapsulating sheet 5 is provided between the liquid permeable topsheet 3 and the absorbent body 4. Thus, an encapsulating sheet 5 having excellent absorbability serves to rapidly distribute the body fluid and to prevent urine and the like from flowing back. The fabric weight per unit area of the pulp is preferably set in a range of 100 $g/m^2$ to 600 $g/m^2$, and further preferably set in a range of 200 $g/m^2$ to 500 $g/m^2$.

For example, a cross-linking polyacrylate, a self-cross-linking polyacrylate, a saponified substance of a cross-linking copolymer of acrylic acid ester and vinyl acetate, a cross-linking substance of a copolymer of isobutylene and maleic anhydride, a cross-linking polysulfonate, and a partially cross-linking substance of a water swellable polymer such as polyethylene oxide and polyacrylamide are cited as examples of the superabsorbent polymer 8. Among the examples, a substance of acryl acid or an acrylate-based substance having a large amount of water absorption and a high absorption speed is preferable. The water-absorbency (water-absorbing ratio) and the water absorption speed of the superabsorbent polymer having the above-mentioned water absorption performance can be adjusted by adjusting the cross-linking density and the cross-linking density gradient in its manufacturing process. The fabric weight per unit area of the polymer is preferably set in a range of 150 $g/m^2$ to 500 $g/m^2$, and further preferably set in a range of 200 $g/m^2$ to 450 $g/m^2$.

Moreover, a synthetic fiber may be mixed into the absorbent body 4. For example, a polyolefin series such as polyethylene or polypropylene, a polyester series such as polyethylene terephthalate and polybutylene terephthalate, and a polyamide series such as nylon, and a copolymer thereof, or a mixture of two kinds thereof, can be used as the synthetic fiber. Furthermore, a composite fiber such as a core-clad type fiber including a core made of a fiber with a high melting point and a clad made of a fiber with a low melting point, a side-by-side type fiber, and a division type, can be also used. When the synthetic fiber is made of a hydrophobic fiber, it is preferable to treat a surface of the synthetic fiber with a hydrophilic agent so as to have hydrophilic properties to the body fluid.

The second sheet 6 just has to have hydrophilic properties to the body fluid. More specifically, a hydrophilic material that has hydrophilic properties in itself can be used as the second sheet 6 by using the regenerated fiber such as rayon and cupra, and the natural fiber such as cotton. Otherwise, a fiber treated to have the hydrophilic properties by treating a surface of a synthetic fiber including an olefin series such as polyethylene and polypropylene, a polyester series, a polyamide series and the like with a hydrophilic agent, can be used. In addition, the second sheet 6 may include a porous film layer on its back side (the absorbent body 4 side) to provide tension, and may be made of a material including pulp.

On both sides of the top surface side of the present incontinence pad 1, side non-woven fabrics 7, 7 are respectively provided along the longitudinal direction over the entire length of the incontinence pad 1, and outer parts of the side non-woven-fabrics 7, 7 extend laterally while the liquid impermeable backsheet 2 extends laterally. Side flaps are formed by attaching the laterally extended side non-wovenfabric 7 parts to the laterally extended liquid impermeable backsheet 2 parts with the hot-melt adhesive and the like.

Either water-repellent non-woven fabric or hydrophilic non-woven fabric is used as the side non-woven-fabric 7 depending on the desired function. For example, when regarding a function of preventing urine and the like from permeating or of improving a texture as important, it is preferable to use the water-repellent non-woven fabric such as SSMS, SMS or SMMS coated with water-repellent agent and the like of a silicon series, a paraffin series and an alkyl chromic chloride series. When regarding the absorbability of the body fluid as important, it is preferable to use a hydrophilic non-woven fabric obtained by making a swellable or porous synthetic fiber by a method of polymerizing the synthetic fiber in the presence of a compound having a hydrophilic group, for example, an oxidation product of polyethylene glycol, in the manufacture of the synthetic fiber, or a method of treating the surface with a metallic salt such as stannic chloride to partially dissolve the surface to form a porous surface and then to precipitate a metallic hydroxide on the surface, and then providing the hydrophilic property for the synthetic fiber by using capillary action. A fiber obtained by processing the natural fiber, the synthetic fiber or the regenerated fiber by a proper processing method is available for the side non-woven-fabric 7.

The side non-woven-fabrics 7, 7 are properly folded to form the standing gathers BS of a double structure including the matched pair of inner standing gathers 10, 10 standing from the neighborhood of the edges of the absorbent body 4 toward the skin side, and the matched pair of outer standing gathers 11, 11 that are located outside the inner standing gathers 10, constituted of the liquid impermeable backsheet 2 extending laterally so as to protrude from the absorbent body 4 and the side non-woven-fabrics 7, and formed so as to stand toward the skin side. Here, the standing gather BS may have a single gather structure constituted of only one of the inner standing gather 10 or the outer standing gather 11, or may not be formed into a standing gather shape standing toward the skin side by just providing the side non-wovenfabric 7 without raising it.

The structure of the inner standing gather 10 and the outer standing gather 11 is described below in more detail. As illustrated in FIG. 2, double sheet parts 7a, 7b are respectively formed on the inner side and the outer side in the width direction by folding both sides of the side non-wovenfabric 7 in the width direction. At least one, in the illustrative example, one threadlike elastic stretchable member 12 is fixed at both ends or proper locations in the longitudinal direction, and is provided inside the double sheet part 7a. At least one, in the illustrative example, two threadlike elastic stretchable members 13, 13 are fixed at both ends or proper locations in the longitudinal direction, and are provided inside the double sheet part 7b. By attaching the base edge portion of the double sheet part 7a on the inner side in the width direction to the upper surface of the liquid permeable topsheet 3 provided on a side portion of the absorbent body 4 with a hot-melt adhesive or the like, and attaching the base edge portion of the double sheet part 7b on the outer side in the width direction to the side edge portion of the liquid impermeable backsheet 2 laterally protruding from the absorbent body 4 with the hot-melt adhesive, the inner standing gather 10 standing toward the skin side is formed of the double sheet part 7a on the inner side in the width direction, and the outer standing gather 11 standing toward the skin side is formed of the double sheet part 7b on the outer side in the width direction. Here, as illustrated in FIG. 3, the side non-woven-fabric 7 does not include the threadlike elastic stretchable members 12, 13 at the end portions in the longitudinal direction, and the double sheet part 7a on the inner side in the width direction is attached to the absorbent body 4 with a hot-melt adhesive.

(About Concave Groove 22)

In the incontinence pad 1, a concave groove 22 that allows body fluids to flow therein is formed at a top surface side of the incontinence pad 1 along the longitudinal direction of the incontinence pad 1. The concave groove 22 receives the body fluid expelled on the surface of the liquid permeable topsheet 3 and temporarily retains the body fluid, while facilitating the diffusion of the body fluid in a front-back direction to increase the absorption speed of the body fluid into the absorbent body 4 and to prevent a side leak of the body fluid.

The concave groove 22 is formed by pre-forming an absorbent body concave portion 20, which is a concave groove or a slit, along the longitudinal direction including the body fluid expelling area at the skin-contacting side of the absorbent body 4 without using compression, and forming an embossed portion 21 in the absorbent body concave portion 20 along the absorbent body concave portion 20 under a status that the liquid permeable topsheet 3 and the second sheet 6, as necessary, are stacked, from the top surface side (skin-contacting side) of the liquid permeable topsheet 3 by the embossing.

Figure 4:
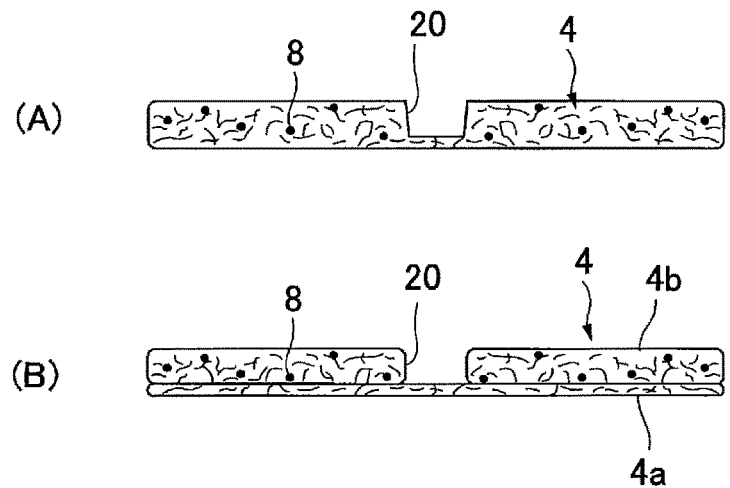
FIG. 4 is a cross-sectional view of an absorbent body 4.

Before forming the embossed portion 21, the absorbent body concave portion 20 is formed in the absorbent body 4 without using compression. The absorbent body concave portion 20 is a non-penetrating type concave groove portion provided with a bottom surface that is concaved from the surroundings toward the non-skin-contacting side (liquid impermeable backsheet 2 side) at a skin-contacting side (liquid permeable topsheet 3 side) surface of the absorbent body 4. Alternatively, instead of such a non-penetrating type, the absorbent body concave portion 20 may be a slit formed to penetrate from the skin-contacting side to the non-skin-contacting side of the absorbent body 4. As illustrated in FIG. 4, for example, the absorbent body concave portion 20 is formed by (A) fiber stacking, (B) stacking an upper layer absorbent body 4b having an opening at a location corresponding to the absorbent body concave portion 20 on a lower layer absorbent body 4a formed as thick as the bottom part of the absorbent body concave portion 20 or the like, without using compression.

As illustrated in FIG. 1, it is preferable that one absorbent body concave portion 20 is formed at the absorbent body 4 at a center portion in the pad width direction and also at a middle portion in the longitudinal direction corresponding to the body fluid expelling area H. Alternatively, a plurality of absorbent body concave portions 20 may be formed with spaces therebetween in the pad width direction, or the absorbent body concave portions 20 may be formed as a discontinuous line with spaces therebetween in the pad longitudinal direction (not illustrated in the drawings). Here, when the plurality of absorbent body concave portions 20 are formed, it is preferable that the embossed portion 21 is formed for each of the absorbent body concave portions 20.

The plane size of the absorbent body concave portion 20 may have a length of 100 to 180 mm in the longitudinal direction of the pad, and may have a groove width of 5 to 30 mm (a groove width at a bottom surface). When the absorbent body concave portion is formed as the concave groove, it is preferable that the depth of the absorbent body concave portion 20 is greater than or equal to 50% of the thickness of the absorbent body 4.

In a part of the absorbent body 4 formed at the bottom of the absorbent body concave portion 20 (part on the liquid impermeable backsheet 2, part on the non-skin side), the mass per unit area of the pulp is set in a range of 70 g/m$^2$ to 210 g/m$^2$, and preferably in a range of 90 g/m$^2$ to 190 g/m$^2$. The mass per unit area of the polymer in the same part is set in a range of 60 g/m$^2$ to 200 g/m$^2$, and preferably in a range of 80 g/m$^2$ to 180 g/m$^2$.

As illustrated in FIG. 2, the concave groove 22 is formed by forming the embossed portion 21 in the absorbent body concave portion 20 along the absorbent body concave portion 20 by the emboss from the skin-contacting side of the liquid permeable topsheet 3.

The embossed portion 21 is integrally formed to the liquid permeable topsheet 3 and the second sheet 6 under a status that the liquid permeable topsheet 3 and the second sheet 6, as necessary, are stacked on the skin-contacting side of the absorbent body 4 by the compression from the skin-contacting side of the liquid permeable topsheet 3. When the absorbent body 4 is surrounded by an encapsulating sheet, the embossed portion 21 may be formed by two steps of compression by which only the encapsulating sheet, that surrounds the absorbent body 4, is previously compressed from a skin-contacting side thereof, and after staking the liquid permeable topsheet 3 and the second sheet 6, as necessary, the liquid permeable topsheet 3 and the second sheet 6 are compressed from the skin-contacting side of the liquid permeable topsheet 3. Alternatively, the embossed portion 21 may be formed by stacking the liquid permeable topsheet 3 and the second sheet 6, as necessary, on the absorbent body 4 surrounded by the encapsulating sheet, and integrally compressing the liquid permeable topsheet 3, the second sheet 6 and the encapsulating sheet from the skin-contacting side of the liquid permeable topsheet 3.

The plane size of the embossed portion 21 may be substantially the same as that of the absorbent body concave portion 20. Specifically, it is preferable that a difference between the width of the embossed portion 21 and the groove width (width of the bottom portion) of the absorbent body concave portion 20 is about 0 to −2 mm. Meanwhile, as variation due to machines are large for the length of the embossed portion 21, it is preferable that the embossed portion 21 is shorter than the length of the absorbent body concave portion 20 about 5 mm to 20 mm. A highly compressed portion, which is compressed lower than the bottom surface of the surrounding concave groove 22, with a desired pattern may be formed at the bottom surface of the embossed portion 21.

By forming the concave groove 22, the following effects can be obtained. By pre-forming the absorbent body concave portion 20 in the absorbent body 4, when the body fluid that has flowed into the concave groove 22 penetrates the absorbent body 4 and the polymer and pulp around the absorbent body concave portion 20 absorb the body fluid and expand, compared with a case that the polymer and pulp that are made to be high density by compression, rising up of the bottom surface of the absorbent body concave portion 20 can be significantly reduced. Further, as the liquid permeable topsheet 3 exists in the absorbent body concave portion 20 by the embossed portion 21, expansion of side surfaces of the absorbent body concave portion 20 can be suppressed to be small. Thus, lowering of the absorbance of the body fluid due to blockage of the absorbent body concave portion 20 by the expanded polymer and pulp that has absorbed the fluid can be prevented. Meanwhile, when the absorbent body concave portion 20 is formed as a slit, as the absorbent body does not exist at the bottom surface of the absorbent body concave portion 20, the bottom surface does not expand when absorbing the fluid.

(Method of Manufacturing Incontinence Pad 1)

In this specification, a method of forming the concave groove 22, which is a specific feature of the embodiment, of a method of manufacturing the incontinence pad 1 is described in detail.

(First Step)

Figure 5:
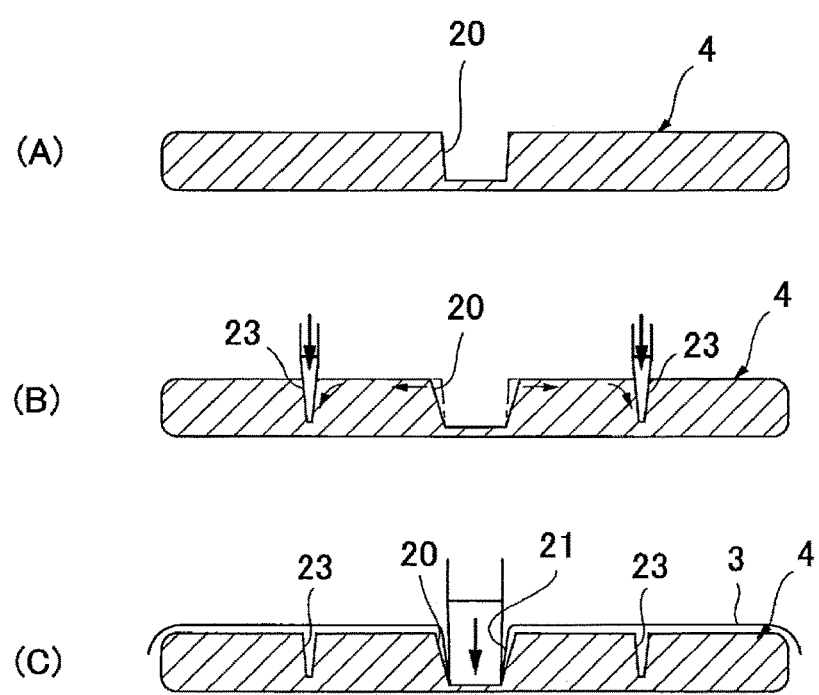
FIG. 5-(A) to (C) are cross-sectional views of a manufacturing step of the incontinence pad 1.

First, in a first step, as illustrated in FIG. 5-(A), the absorbent body 4 provided with the absorbent body concave portion 20 is formed by the fiber stacking or the stacked structure as illustrated in the described FIG. 4.

(Second Step)

Next, in a second step, as illustrated in FIG. 5-(B), core embosses 23 with predetermined patterns are formed at least on both sides of the absorbent body concave portion 20 by the compression from the skin-contacting side of the absorbent body 4. When the absorbent body 4 is surrounded by an encapsulating sheet, the core embosses 23 may be formed in the absorbent body 4 before being surrounded by the encapsulating sheet, or the core embosses 23 may be formed in the absorbent body 4 surrounded by the encapsulating sheet by the compression from a skin-contacting side of the encapsulating sheet. The core embosses 23 may be formed in various shapes. The core embosses 23 will be explained later in detail.

By forming the core embosses 23 in the absorbent body 4, as illustrated in FIG. 5-(B), as fibers are pulled inside the core emboss 23, both side walls of the absorbent body concave portion 20 are inclined toward the outside, and the opening of the absorbent body concave portion 20 can be widened.

(Third Step)

Thereafter, as a third step, as illustrated in FIG. 5-(C), the liquid permeable topsheet 3 and the second sheet 6, as necessary, are stacked on the skin-contacting side of the absorbent body 4 at which the core embosses 23 are formed, and the embossed portion 21 is formed along the absorbent body concave portion 20 in the absorbent body concave portion 20.

At this time, by forming the core embosses 23 in the second step, the opening of the absorbent body concave portion 20 is enlarged, a front end portion of an embossing machine used to form the embossed portion 21 can be securely introduced inside the absorbent body concave portion 20 without compressing unnecessary portions of the absorbent body 4. With this, the absorbent body 4 and the embossing machine can be easily aligned so that the concave groove 22 can be easily processed, and the concave groove 22 can be properly formed without compressing unnecessary portions.

(Core Emboss 23)

Figure 6:
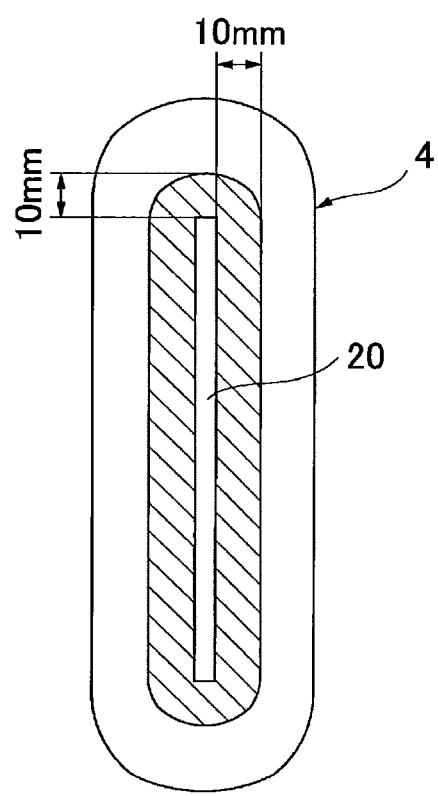
FIG. 6 is a plan view of the absorbent body 4.

It is preferable that the core embosses 23 are formed at positions apart from the absorbent body concave portion 20 for a predetermined distance. Specifically, as illustrated in FIG. 6, the core embosses 23 are formed at a distance range from the edge portion of the absorbent body concave portion 20 that is greater than or equal to 10 mm and less than or equal to 30 mm, preferably, greater than or equal to 10 mm and less than or equal to 25 mm. If the core embosses 23 are formed at a distance from the absorbent body concave portion 20 that is less than 10 mm, in other words, within a hatched range in the drawing, the height of the side walls of the absorbent body concave portion 20 (the depth of the absorbent body concave portion 20) is reduced due to pulling by the core embosses 23, which reduces the volume of the concave groove 22 and there is a risk that absorbance of the body fluid is lowered. On the other hand, if the core embosses 23 are formed at a distance from the absorbent body concave portion 20 that is greater than 30 mm, it is not preferable because the effect of tilting the side walls of the absorbent body concave portion 20 outward may be reduced. The distance from the edge portion of the absorbent body concave portion 20 is a minimum linear length between the edge portion of the core emboss 23 and the edge portion of the absorbent body concave portion 20.

The core emboss 23 may be formed to have various plane shape patterns. For the example illustrated in FIG. 1, the core embosses 23 are formed on both sides of the absorbent body concave portion 20. Each of the core embosses 23 is formed as a continuous linear line pattern along the longitudinal direction of the pad, including a range that overlaps the absorbent body concave portion 20 in the width direction of the pad. By forming the core embosses 23 with a length greater than or equal to the length of the absorbent body concave portion 20, including the range that overlaps the absorbent body concave portion 20 in the pad width direction, the absorbent body concave portion 20 can be opened over its entirety in the longitudinal direction.

Figure 7:
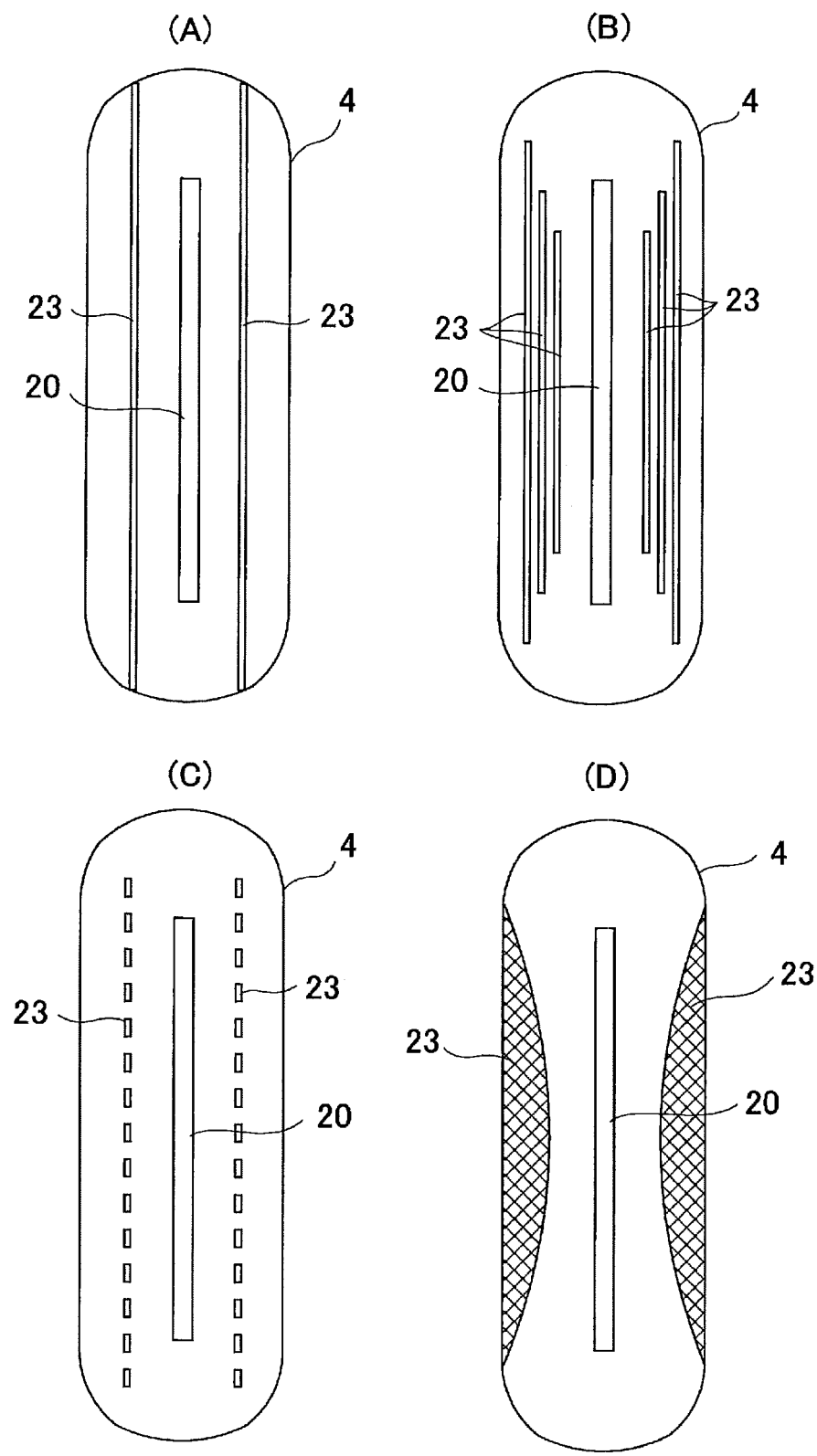
FIG. 7-(A) to (D) are plan views of the absorbent body 4.

Although the linear pattern is formed at the middle of the absorbent body 4 in the longitudinal direction for the example illustrated in FIG. 1, as illustrated in FIG. 7-(A), the core emboss 23 may be formed over the entire length of the absorbent body 4. With this, diffusion of the body fluid from the center portion to the core embosses 23 can be improved over the entire length of the absorbent body 4.

Further, although a single core emboss 23 is formed on both sides of the absorbent body concave portion 20 in FIG. 1, as illustrated in FIG. 7-(B), a plurality of core embosses 23 that are apart from each other in the width direction of the pad may be formed on both sides of the absorbent body concave portion 20. In the illustrated example, three core embosses 23 are formed on both sides of the absorbent body concave portion 20. When a plurality of the core embosses 23 are formed, all of them may be formed to have the same length, or as the illustrated example, the inside core emboss 23 may be formed such that the length of the core embosses 23 may be progressively reduced at front and rear toward inside. Here, at least one of the core embosses 23 is formed to have at least the same length as the absorbent body concave portion 20 to be overlap in the pad width direction. By forming the plurality of core embosses 23, the absorbent body concave portion 20 can be clearly opened, and as highly compressed area is formed over a broader range, the diffusion of the body fluid can be furthermore improved. When forming a plurality of core embosses 23, the plurality of core embosses 23 may be compressed at the same time. However, alternatively, in order to easily obtain the effect of pulling both side walls of the absorbent body concave portion 20 outward, the core embosses 23 may be formed from the outer side to the inner side in this order.

Further, as illustrated in FIG. 7-(C), the core emboss 23 may be formed as a discontinuous line pattern in which a plurality of compressed portions and a plurality of non-compressed portions are alternatively formed in the longitudinal direction of the pad. For this pattern, although the effects of opening the absorbent body concave portion 20 or the diffusion of the body fluid by the compression are somewhat reduced, stiffening of the absorbent body due to forming the core embosses 23 can be suppressed.

Further, as illustrated in FIG. 7-(D), the core emboss 23 may be formed as a curved pattern. In the illustrated example, the core emboss 23 is formed in an arc pattern that protrudes inwardly. Here, although the entirety of the area that is continued to an end portion of the absorbent body 4 in the pad width direction is compressed in the illustrated example, the core emboss 23 may be formed by one or a plurality of curved patterns that substantially extends along the longitudinal direction of the pad.

As illustrated in FIG. 7-(D), the core emboss 23 may be formed to be compressed over the entirety of the area that is continued to the end portion of the absorbent body 4 in the pad width direction. With this, the effect of the core emboss 23 can be further more clearly obtained and as both side portions of the absorbent body 4 are thinner, fittability is improved.

Although not illustrated in the drawings, the core emboss 23 may further be formed in various patterns, such as a dot-like pattern in which a plurality of dots are formed in a predetermined area, a grid-like pattern in which a plurality of pad longitudinal direction lines and pad width direction lines are crossed with each other, or the like.

Figure 8:
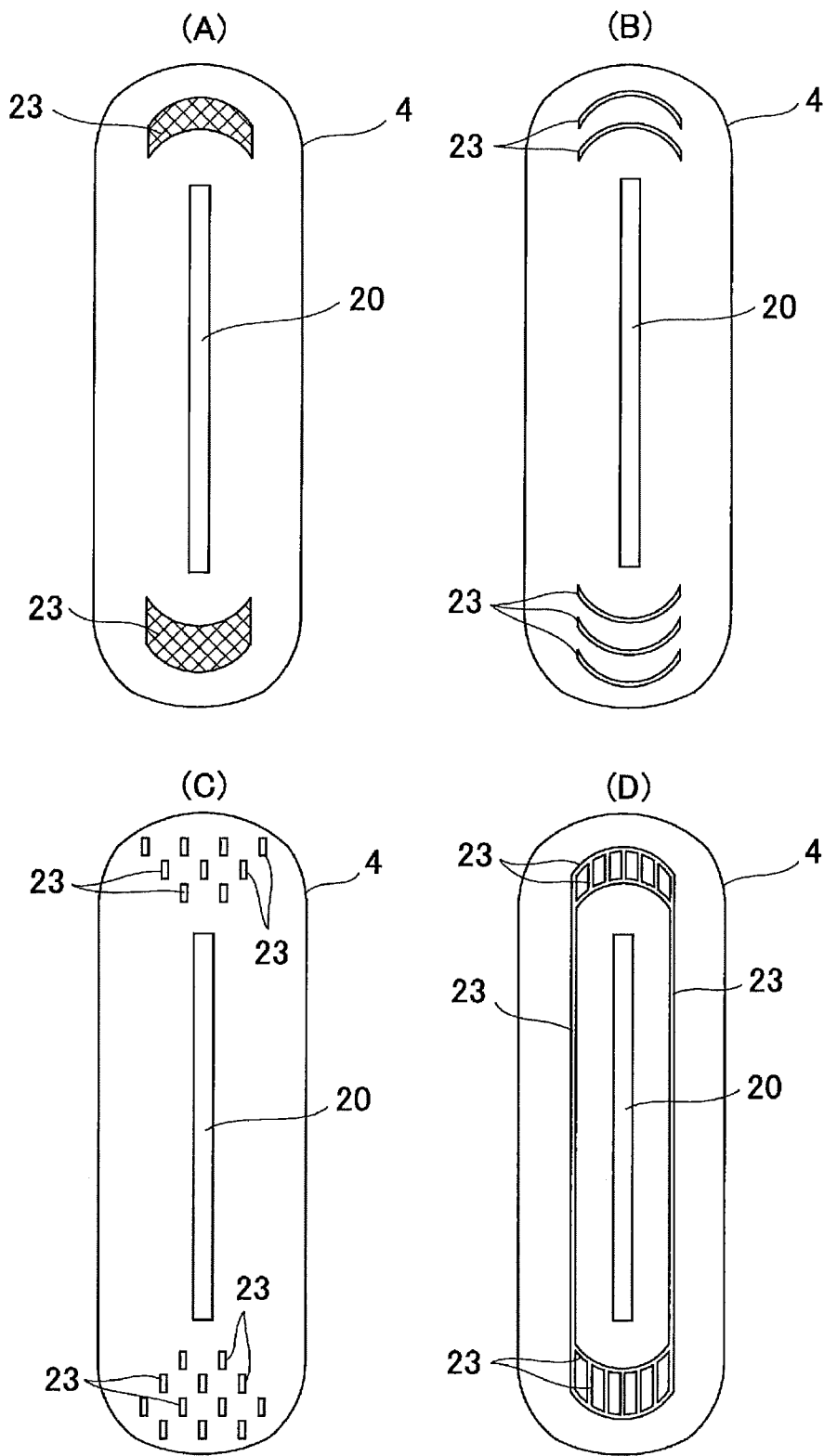
FIG. 8-(A) to (D) are plan views of the absorbent body 4.

As illustrated in FIG. 8, the core embosses 23 may be formed at a front side and a rear side of the absorbent body concave portion 20, not only on both sides of the absorbent body concave portion 20. For a case of a vertical direction flow in which the machine is moved in the longitudinal direction of the pad, the core embosses 23 at the front and rear portions of the absorbent body concave portion 20 are not necessarily formed from the view point of improving the accuracy of finishing of the embosses because variation of the movement of the machine with respect to the core embosses 23 at the front and rear portions of the absorbent body concave portion 20 is large. However, it is preferable to form the core embosses 23 at the front and rear portions of the absorbent body concave portion 20 from the view point that the body fluid can be absorbed with less pulp or polymer because the diffusion to the front and rear directions of the absorbent body concave portion 20 is improved and the entirety of the absorbent body can be effectively used.

Examples of the plane shapes of the core embosses 23 formed at the front and rear parts of the absorbent body concave portion 20 are illustrated in FIG. 8. In FIG. 8, (A) illustrates a pattern in which the entirety of an area defined by an arced shape each of whose front and rear edges protrudes outward in the pad longitudinal direction is compressed. In FIG. 8, (B) illustrates a pattern that substantially extends along the pad width direction, and is composed of one or a plurality of curves that protrude outward in the pad longitudinal direction. In FIG. 8, (C) illustrates a pattern in which a plurality of compressed portions are placed in a staggered or a grid-like manner with spaces therebetween in the longitudinal direction of the pad and across the width direction of the pad. In FIG. 8, (D) illustrates a pattern in which two arcs that extend across the pad width direction and protrude outward in the longitudinal direction of the pad are spaced apart in the longitudinal direction of the pad. Further, the two arcs are connected by a plurality of linear lines that extend along longitudinal direction of the pad and spaced apart from each other in the width direction of the pad.

The core embosses 23 at the front and rear parts of the absorbent body concave portion 20 may be formed to be continuous from the core embosses 23 formed on both sides of the absorbent body concave portion 20 (see FIG. 8-(D)), or may be formed with spaces therebetween.

As illustrated in FIG. 7-(B), FIG. 7-(D) and FIG. 8, when the core emboss 23 is continuously or discontinuously formed from the absorbent body concave portion 20 side to the outer side, the compression pressure may be constant over the entire area, or the compression pressure may be set such that the compression pressure of the core emboss 23 at the outer side gradually increases continuously or stepwisely from the compression pressure of the core emboss 23 at the inner side. By gradually increasing the compression pressure toward the outer side, the density gradient of fibers is formed by which the density of the absorbent body 4 gradually increases toward the outer side. As a result, the diffusion of the body fluid is further increased, volume of retaining the body fluid by the absorbent body 4 can be effectively utilized to the maximum without increasing the amount of pulps or polymers, and the absorbance can be improved.

1 incontinence pad
2 liquid impermeable backsheet
3 liquid permeable topsheet
4 absorbent body
6 second sheet
7 side non-woven-fabric
8 superabsorbent polymer
10 inner standing gather
11 outer standing gather
12, 13 threadlike elastic stretchable member
20 absorbent body concave portion
21 embossed portion
22 concave groove
23 core emboss

What is claimed is:

1. A method of manufacturing an absorbent article in which an absorbent body is provided between a liquid permeable topsheet and a backsheet,
the method comprising:
a first step of forming the absorbent body provided with an absorbent body concave portion, which is a concave groove or a slit, being formed at a skin-contacting side including a body fluid expelling area along a longitudinal direction of the absorbent body without using compression, said skin-contacting side being arranged to contact a skin of a user when being worn by the user, said absorbent body including a lower layer that is a flat absorbent sheet without the absorbent body concave portion and an upper layer that is provided on the lower layer and has the absorbent body concave portion, said lower layer and upper layer being formed of a same material;
a second step of forming a first and second core embosses on both sides of the absorbent body concave portion in a width direction, respectively, by compressing the absorbent body from the skin-contacting side of the absorbent body, the width direction being substantially perpendicular to the longitudinal direction; and
a third step of stacking the liquid permeable topsheet on the skin-contacting side of the absorbent body and forming a concave groove in the absorbent body concave portion along the absorbent body concave portion by embossing the liquid permeable topsheet from a skin-contacting side of the liquid permeable topsheet,
the first step, the second step and the third step being performed in this order,
wherein the absorbent body concave portion has a slanted side wall so that an opening portion of the absorbent body concave portion is wider than a bottom portion of the absorbent body concave portion when the absorbent body is placed on a flat surface.

2. The method of manufacturing the absorbent article according to claim 1, wherein each of the first and second core embosses is formed at a distance range from an edge portion of the absorbent body concave portion in the width direction that is greater than or equal to 10 mm and less than or equal to 30 mm.

3. The method of manufacturing the absorbent article according to claim 1, wherein the plane shape of each of the first and second core embosses is a pattern of one or a plurality of continuous lines or discontinuous lines, or dots or a grid-like shape along a longitudinal direction of the absorbent article.

4. The method of manufacturing the absorbent article according to claim 1, wherein the first and second core embosses are also formed at a front side and a rear side of the absorbent body concave portion in the longitudinal direction.

5. The method of manufacturing the absorbent article according to claim 1, wherein each of the first and second core embosses is continuously or discontinuously formed from an absorbent body concave portion side toward an outer side in a plan view, and the compression pressure is set such that the compression pressure gradually increases toward the outer side.

6. The method of manufacturing the absorbent article according to claim 1, wherein in the first step, the absorbent body concave portion is formed in the absorbent body such that a part of the absorbent body exists at a bottom surface of the absorbent body concave portion.

7. The method of manufacturing the absorbent article according to claim 1, wherein in the third step, the liquid permeable topsheet is not embossed into the first and second core embosses.

8. The method of manufacturing the absorbent article according to claim 1, further comprising forming standing gathers including an inner standing gather and an outer standing gather provided at a periphery of the absorbent body, at least a protruding portion of the inner standing gather and the outer standing gather extending away from the absorbent body.

9. The method of manufacturing the absorbent article according to claim 8, wherein the inner standing gather includes a base portion and the protruding portion, said base portion being attached to the liquid permeable topsheet so as to extend from the periphery of the liquid permeable topsheet toward the absorbent body concave portion, said protruding portion being formed by folding the inner standing gather away from the absorbent body.

10. The method of manufacturing the absorbent article according to claim 1, wherein each of the first and second core embosses extends so as to cover an entire length of the absorbent body in the longitudinal direction of the absorbent body.

11. The method of manufacturing the absorbent article according to claim 1, wherein both the lower and upper layers include absorbent fiber.

* * * * *